United States Patent [19]

Stewart et al.

[11] Patent Number: 5,720,741
[45] Date of Patent: Feb. 24, 1998

[54] VENOUS RESERVOIR BAG ASSEMBLY

[75] Inventors: Rodger L. Stewart, Lafayette; William D. Dalke, Aurora; Joseph A. Scibona, Littleton; Barry D. Reed, Longmont, all of Colo.; John T. Buckley, Newark, Calif.

[73] Assignee: Cobe Laboratories, Inc., Lakewood, Colo.

[21] Appl. No.: 481,752

[22] Filed: Jun. 7, 1995

Related U.S. Application Data

[62] Division of Ser. No. 190,309, Feb. 2, 1994, Pat. No. 5,693,039, which is a continuation of Ser. No. 725,126, Jul. 3, 1991, Pat. No. 5,352,218, which is a continuation-in-part of Ser. No. 538,903, Jun. 15, 1990, abandoned.

[51] Int. Cl.$^6$ .................................................. A61J 1/05
[52] U.S. Cl. ........................... 604/407; 604/408; 222/95
[58] Field of Search .................... 604/407–9, 246, 604/251, 260, 262, 4, 182; 222/92, 95, 103

[56] References Cited

U.S. PATENT DOCUMENTS

| | | | |
|---|---|---|---|
| 3,366,276 | 1/1968 | Fridley | 222/51 |
| 3,565,292 | 2/1971 | Jinotti | 222/103 |
| 3,595,232 | 7/1971 | Leibinsohn | 128/214 |
| 3,625,401 | 12/1971 | Terry | 222/103 |
| 3,642,047 | 2/1972 | Waage | 150/8 |
| 3,734,351 | 5/1973 | Gaudin | 222/103 |
| 3,777,697 | 12/1973 | Woessner | 604/262 |
| 3,902,635 | 9/1975 | Jinotti | 222/103 |
| 3,907,504 | 9/1975 | Hammond et al. | 23/258.5 |
| 3,942,529 | 3/1976 | Waage | 128/272 |
| 3,992,706 | 11/1976 | Tunney et al. | 340/239 R |
| 4,004,590 | 1/1977 | Muriot | 128/276 |
| 4,019,656 | 4/1977 | Spears | 222/103 |
| 4,019,707 | 4/1977 | Quinn et al. | 248/95 |
| 4,058,363 | 11/1977 | Silbert | 21/58 |
| 4,085,866 | 4/1978 | Fekl | 222/158 |
| 4,157,771 | 6/1979 | Smith | 222/103 |
| 4,187,845 | 2/1980 | Dror | 128/205 |
| 4,284,209 | 8/1981 | Barbour, Jr. | 222/1 |
| 4,316,576 | 2/1982 | Cullis et al. | 233/26 |
| 4,378,014 | 3/1983 | Elkow | 128/214 |
| 4,393,880 | 7/1983 | Taylor | 604/322 X |
| 4,447,939 | 5/1984 | Taylor | 604/322 X |
| 4,451,259 | 5/1984 | Geissler et al. | 604/408 |
| 4,496,354 | 1/1985 | Steer et al. | 604/322 |
| 4,500,311 | 2/1985 | Redmon et al. | 604/326 |
| 4,529,102 | 7/1985 | Quinn et al. | 604/410 |
| 4,557,728 | 12/1985 | Sealfon et al. | 604/134 |

(List continued on next page.)

FOREIGN PATENT DOCUMENTS

| | | |
|---|---|---|
| 0 093 982 A1 | 5/1982 | European Pat. Off. . |
| 0 342 404 A2 | 5/1988 | European Pat. Off. . |
| 0 198 869 B1 | 12/1988 | European Pat. Off. . |
| 1408360 | 7/1964 | France . |
| 2102412 | 3/1972 | France . |
| 2584608 | 7/1985 | France . |
| 27 21 824 A1 | 5/1977 | Germany . |
| 61-257659 | 11/1986 | Japan . |
| 63-189161 | 8/1988 | Japan . |
| 2-119869 | 5/1990 | Japan . |
| 7708421 | 2/1978 | Netherlands . |
| WO 94/08645 | 4/1994 | WIPO . |

OTHER PUBLICATIONS

Deknatel, Pleue–Evvc Auto Transfusion System, 1986.

*Primary Examiner*—David H. Willse
*Assistant Examiner*—Bruce E. Snow
*Attorney, Agent, or Firm*—Holme Roberts & Owen

[57] ABSTRACT

A venous reservoir bag subassembly is provided which is adapted to cooperate with a mounting assembly having a bracket frame and a front plate reproducibly relatively movable to enable constant accurate blood volume readout, cooperating means between the subassembly and the mounting assembly to provide against unduly low blood volume, and angled conduit means cooperating with the bag and recesses in the subassembly and assembly to provide further failsafe against passage of the undesirable gas.

17 Claims, 4 Drawing Sheets

U.S. PATENT DOCUMENTS

| | | | |
|---|---|---|---|
| 4,626,243 | 12/1986 | Singh et al. | 604/141 |
| 4,642,089 | 2/1987 | Zupkas et al. | 604/4 |
| 4,650,452 | 3/1987 | Jensen | 493/206 |
| 4,976,851 | 12/1990 | Tanokura et al. | 210/86 |
| 4,991,743 | 2/1991 | Walker | 604/132 |
| 5,049,146 | 9/1991 | Bringham et al. | 604/4 |
| 5,061,236 | 10/1991 | Sutherland et al. | 604/4 |
| 5,061,451 | 10/1991 | Ganshirt et al. | 422/101 |
| 5,078,677 | 1/1992 | Gentelia et al. | 604/4 |
| 5,238,582 | 8/1993 | Hori et al. | 210/749 |
| 5,262,070 | 11/1993 | Ishida | 604/408 |

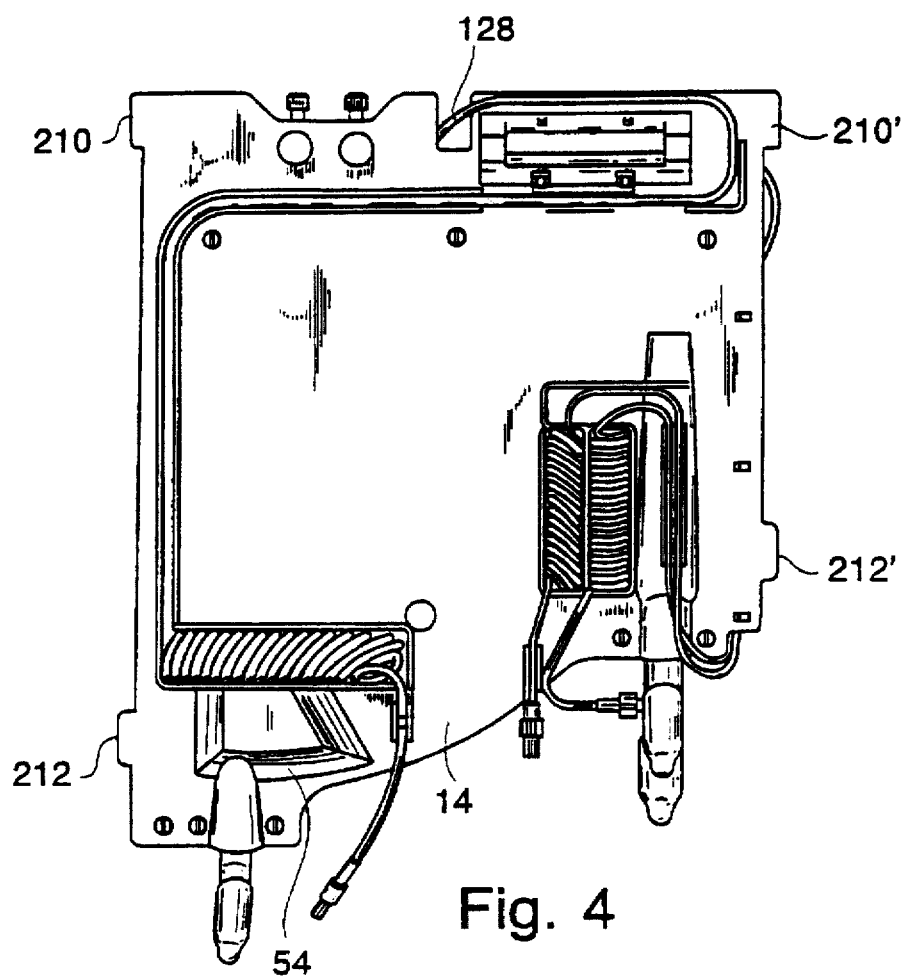
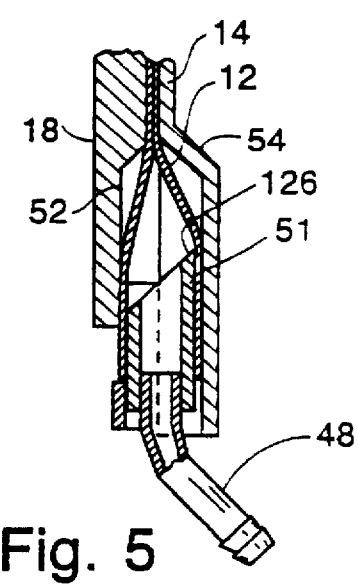
Fig. 5
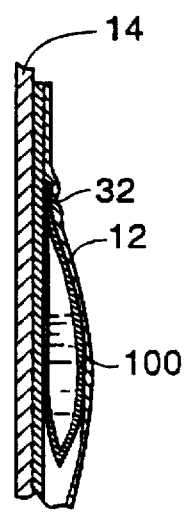
Fig. 6

VENOUS RESERVOIR BAG ASSEMBLY

RELATED APPLICATIONS

This is a divisional of application Ser. No. 08/190,309, filed Feb. 2, 1994, now U.S. Pat. No. 5,693,039 which is a continuation of application Ser. No. 07/725,126, filed Jul. 3, 1991, now U.S. Pat. No. 5,352,218 which is a continuation-in-part of application Ser. No. 07/538,903, filed Jun. 15, 1990, now abandoned.

FIELD OF THE INVENTION

This invention relates to extracorporeal body fluid reservoirs used to store body fluids during surgical procedures, and more particularly to venous reservoir closed bag assemblies useful for extracorporeal storing of blood from a patient (e.g., in cardiopulmonary bypass procedures).

BACKGROUND OF THE INVENTION

In many surgical procedures blood is removed from a patient and passed through an extracorporeal circuit. For example, during open heart surgery blood may be directed into an extracorporeal circuit for oxygenation and filtration. The blood diverted from the patient's body is stored temporarily in at least one extracorporeal reservoir, typically called a venous reservoir.

There are two general types of known venous reservoirs: open reservoirs and closed reservoirs. Open reservoirs typically comprise a rigid shell into which blood is directed during surgery and accumulates from the bottom up. The reservoir may include a calibrated scale to allow an operator, or perfusionist, to readily determine the volume content of blood in the reservoir. However, open venous reservoir systems currently employed do not provide for the automatic detection of low blood levels in a reservoir.

In open reservoirs an air to blood interface typically exists along the top surface of the blood in the reservoir. As such, gas bubbles within the blood can migrate upward in the reservoir and escape. However, prolonged exposure of the blood near the surface may damage components of the blood.

Closed reservoirs typically are closed bags formed from plastic or other non-porous material which deforms under pressure. These bags may be suspended from a stand located near the patient. Blood is typically directed into the bottom of the bag through an inlet tube and exits the bag through an outlet tube located near the bottom of the bag. Because the bag deforms irregularly under pressure, closed reservoirs are not easily calibrated to reflect the volume of blood contained therein. Further, closed venous reservoir systems currently employed do not accommodate reliable low level blood detection.

Closed reservoirs typically have no blood to air interface as is common with open reservoirs. Therefore, closed reservoirs largely avoid blood damage caused by prolonged exposure of blood to air. However, gas bubbles may become entrapped within the contained blood because they cannot migrate upward to a blood to air interface. To alleviate this problem, reservoirs have been designed to include screen filters which remove gas bubbles from the blood. The gas bubbles may, for example, be vented from the bag through a vent located near the top of the bag.

SUMMARY OF THE INVENTION

Objects of the present invention are to provide a venous reservoir assembly wherein the receipt and dispensation of body fluid within a flexible reservoir is effected in a manner that allows for reliable volume determination, low level detection, gas bubble removal, and the realization of related advantages.

To meet the aforementioned objectives, we have mounted a flexible venous reservoir bag on a rigid plate to provide a closed bag and bag plate subassembly. This subassembly is desirably releasably latchable into a support assembly having a back support portion ("bracket frame") and a front portion ("front plate"), the portions being relatively movable in a constant spaced relationship to predeterminedly vary the instantaneous thickness (and thus volume) of the bag in a constant manner.

There is provided a closed bag system which is easy to use, with easy air handling and simplified accurate contents volume resolution.

BRIEF DESCRIPTION OF THE DRAWINGS

FIG. 4 is a rear elevation view of the bag plate of the embodiment.

FIG. 5 is a sectional view taken at 5—5 of FIG. 2.

FIG. 6 is a sectional view taken at 6—6 of FIG. 2.

DETAILED DESCRIPTION

Figure 1:
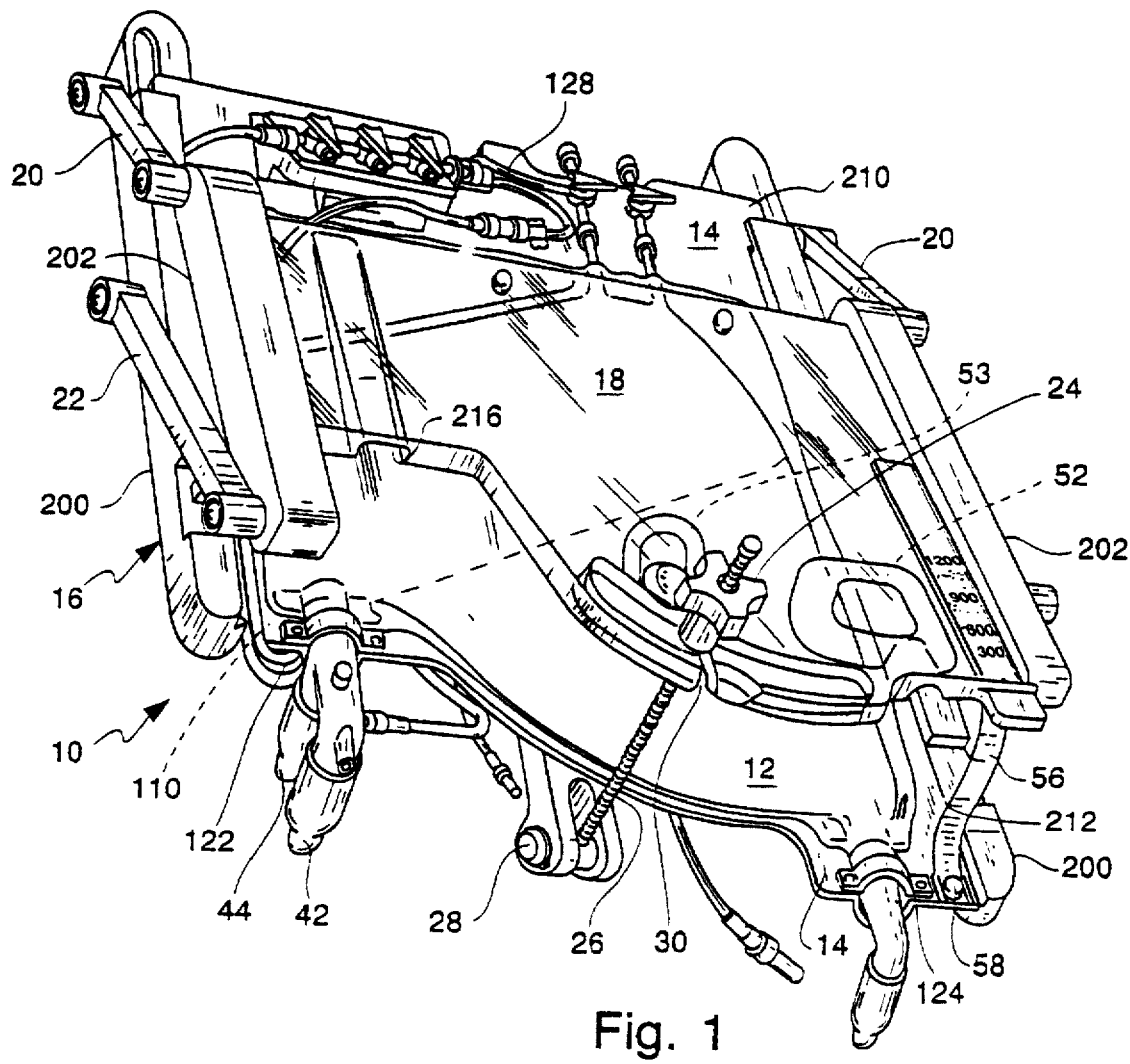
FIG. 1 is a perspective view of one embodiment of the disclosed invention showing the front portion adjacent the back portion and the volume-limiting nut stop in one position.

Referring now to FIG. 1, there is shown, in the embodiment indicated generally at 10, a subassembly comprising a closed flexible bag 12 (e.g. having a 1200 ml. capacity) and bag plate 14 seated in a support assembly between its bracket frame 16 and its front, or upper, plate 18.

Figure 3:
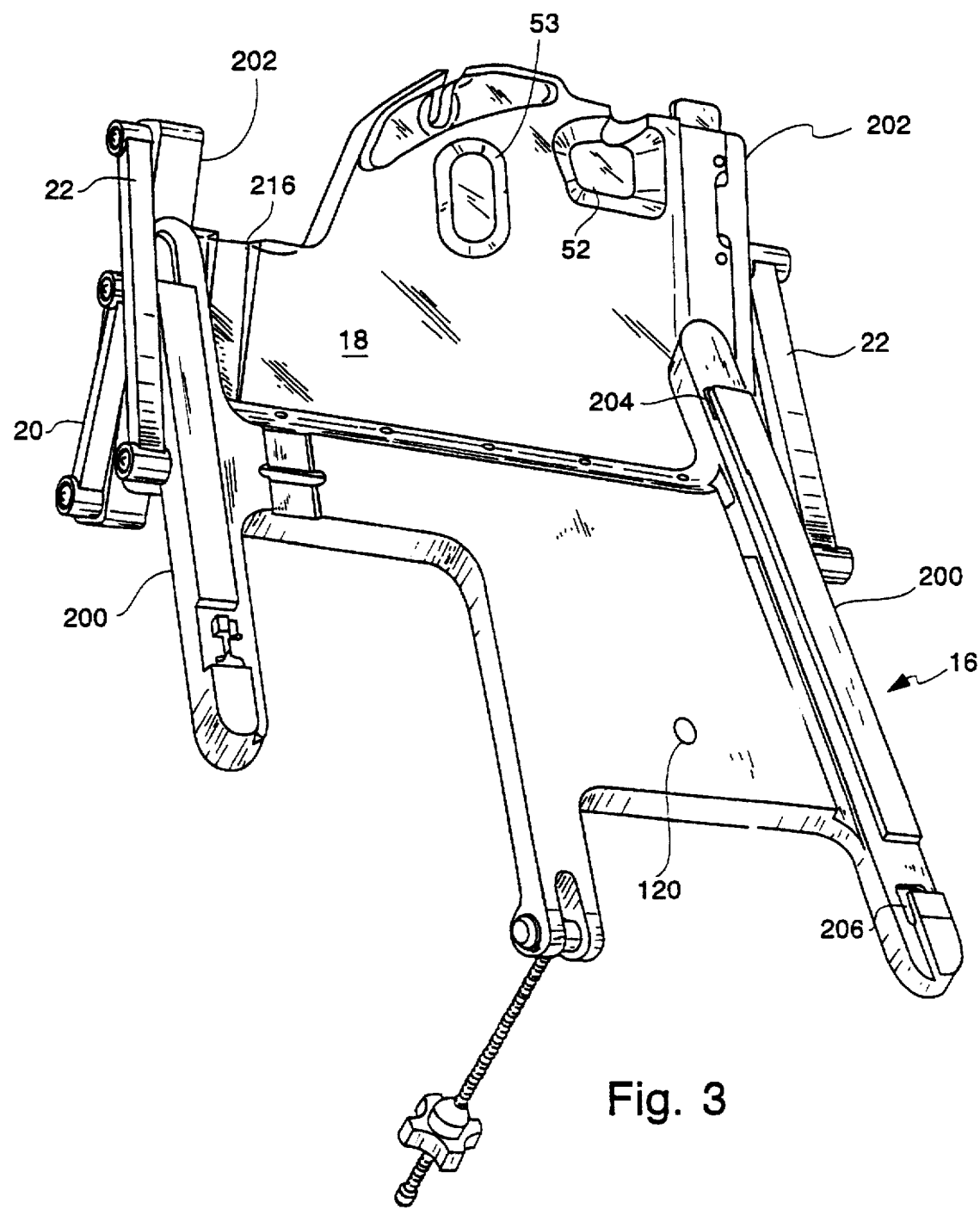
FIG. 3 is a perspective view of the support assembly of the embodiment with the bag and plate subassembly removed.

As best shown in FIG. 3, bracket frame 16 of the illustrated embodiment is a substantially planar structure having side edges 200. Similarly, upper plate 18 is substantially planar and is secured to side edges 202. Bracket frame 16 and upper plate 18 are interconnected by two pairs of pivotal arms 20, 22 along side edges 200 and 202. Bracket frame 16 is dimensioned to receive bag plate 14 and includes slots (e.g. 204, 206 as best shown in FIG. 3) for receiving tabs (e.g. 210, 210', 212, 212' as best shown in FIG. 4) on bag plate 14 to retain bag plate 14 in a fixed position with respect to bracket frame 16.

Figure 2:
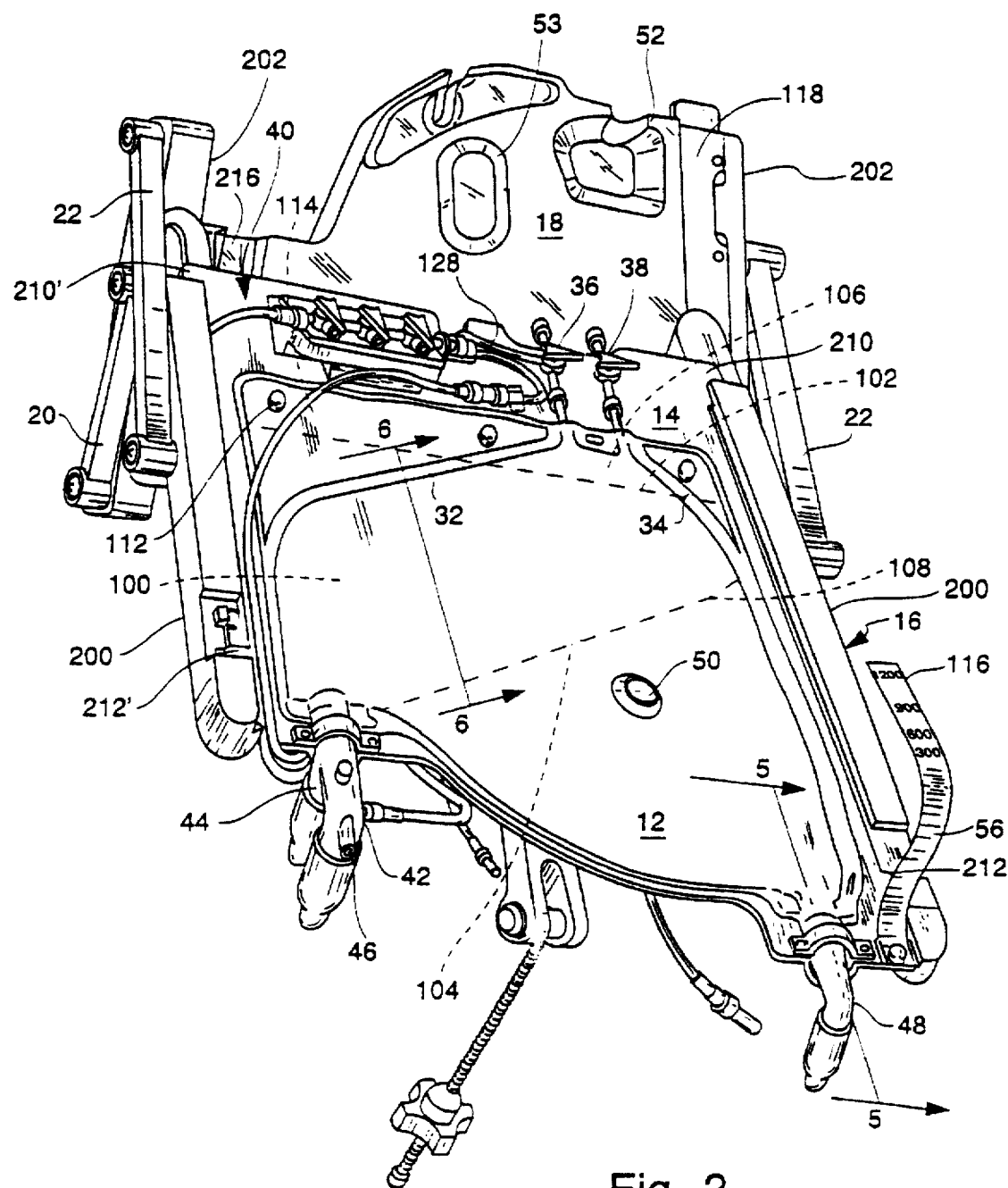
FIG. 2 is a perspective view of said embodiment showing the front portion moved away from the back portion.

Upper plate 18 is of a predetermined weight (e.g. approximately two pounds) and in the illustrated embodiment is connected with bracket frame (back plate) 16 by a pair of shorter arms 20 and a pair of longer arms 22. Each arm 20 and 22 is pivotally secured toward its back end to bracket frame 16 and toward its front end to front plate 18, in a relationship such that at one travel extremity, as shown in FIG. 1, the plates 16 and 18 are nearly parallel, while at the other travel extremity, as shown in FIG. 2, plates 16 and 18 are widely separated. At the first mentioned travel extremity, plates 16 and 18 are spaced to permit a predetermined volume (e.g. about 200 ml.) of blood to enter before the volume of blood begins to move front plate 18.

As best illustrated in FIGS. 2 and 3, the upper plate 18 includes a substantially flat lower surface having a first recess 52 and a second recess 216. In operation, the lower surface of plate 18 contacts the upper surface of bag 12. As the bag 12 fills with blood, pressure from the blood forces upper plate 18 away from lower plate 14 while the substantially parallel relationship therebetween is maintained. The flat lower surface of plate 18 causes the upper surface of bag 12 to remain substantially flat as the bag fills with blood.

The maximum distance between plates 16 and 18, and thus the maximum volume of bag 12, can be set by means of nut 24, which is threadedly carried by member 26 for uninterrupted continuously variable distance settings therealong, the member 26 being mounted for pivotal movement about pivot 28 carried by bracket frame 16, and engageable in slot 30 of front plate 18 to act as a stop therefor.

The bracket frame 16 is mounted (on pole means not shown) to support the bag and bag plate at an angle (e.g. 45°, or even more preferred, 55°) to the horizontal, the end of bag plate 14 at outlet 48, alongside the bottom of bag 12, being the lower end thereof.

Bag plate 14 carries bag 12 as well as the outlets 36, 38, and the blood gas sample system 40. As best illustrated in FIGS. 4 and 5, bag plate 14 also includes recess 54 positioned adjacent to outlet tube 51. Recesses 52 and 54 cooperate to form a chamber which surrounds outlet tube 51 when front plate 18 and bag plate 14 are substantially adjacent.

Bag 12 is a flat bag formed of two layers of flexible vinyl sheet 114 RF welded around the periphery as at 32, 34. Bag 12 includes an inlet tube 110 and an outlet tube 51 disposed to allow the flow of blood into and out of reservoir 12, respectively. A woven polyester fabric (105μ apertures) double layer element 100 disposed between the vinyl layers aids in removing gas. This fabric element is secured in the above-mentioned RF weld above which it extends to the pair of edges 102, and is folded along edge 104. Disposing element 100 in this manner requires blood entering the reservoir through inlet tube 110 to flow through element 100 before exiting the reservoir through outlet tube 51. Gas bubbles removed by screen element 100 may be vented from the bag through gas outlets 36 and 38.

There are two bypass regions around the screen within the bag. One is the area 106 at the very top of the screen in the region of the vent lines to outlets 36, 38. Heat seal 32 does not extend through fabric layers 100 here. This bypass 106 is to facilitate removal of air from both sides of the screen. The other screen bypass 108 is located at the right-most part of the screen, farthest away from the venous inlet, a triangular portion of the double thickness of which is cut away. This is a safety bypass to minimize the possibility of pushing air through the screen in the extreme condition of running at very low reservoir volumes, and having a large amount of air collected in the screen without venting through the top of the bag. It also provides a bypass around the screen, in the event the screen should become occluded.

Bag 12 includes as portions of it venous inlet 42, cardiotomy inlet 44, temperature probe 46, outlet 48, vent line 128 and magnet 50. Inlet 110, into which inlets 42 and 44 feed, is secured between the two layers of fabric element 100 within bag 12. Inlet tube 110 and outlet tube 51 are secured for immovability and thus strain relief with prevention of bag twisting in use by respectively clamps 122 and 124 secured to bag plate 14. The rigid bag plate 14 is of white plastic for contrast with blood level during use.

Insurance against drawing blood down too far with possible air entrapment is provided by the combination of magnet 50, mounted on the outer surface of bag 12 toward front plate 18, and a normally open reed switch sensor, carried by bracket frame 16 in hole 120 just below magnet 50 (e.g. protruding 0.100 inches above the surface of bracket frame 16) toward bag 12. When the volume of blood in bag 12 drops to a sufficiently low level, magnet 50 triggers the reed switch sensor to terminate operation. Front plate 18 includes recess 53 for receiving magnet 50.

A second shut off system is illustrated in FIG. 5. As discussed above, recess 52 in upper plate 18 and recess 54 in lower plate 14 form a chamber surrounding outlet tube 51, which is integrally attached to the walls of bag 12.

The outlet connector 48 is inserted into outlet tube 51 with an upper surface 126 at an angle.(e.g. 45°) to the direction of blood flow and generally to the wall of bag 12. As illustrated in FIG. 5, as reservoir 12 empties upper plate 18 and lower plate 14 are substantially adjacent to one another and the remaining blood is collected in the chamber defined by recesses 52 and 54. As this chamber empties, the upper wall of reservoir 12 collapses over angled surface 126 of outlet tube 51, thereby restricting air flow through tube 51. This provides positive shutoff when the reservoir is emptied of fluid, the bag top surface moving appropriately against the angled surface.

Pockets 52 and 54 keep the walls of bag 12 away from outlet tube 51 to prevent possible premature shutoff of blood flow.

Volume readout is provided by virtue of flexible tape 56, which bears indicia 116 as shown in the drawings, has its lower extremity 58 anchored in bag plate 14, and has its upper portions moving in a slot 118 in upper plate 18. As noted above, upper plate 18 moves up and down within its predetermined range of motion in response to changes in volume of blood in reservoir 12. Flexible tape 56 is calibrated to reflect the volume of reservoir 12 as a function of the distance between upper plate 18 and lower plate 14.

Operation

In operation, a flexible reservoir bag 12 is secured to the lower plate 14 using connectors 112 and clamps 122 and 124. The lower plate 14 is then secured to the lower bracket structure 200 by sliding tabs (e.g., 210 and 212) into complimentary slats (e.g., 204 and 206). The assembly 10 is then disposed at an angle with respect to the horizontal such that gas vents 36, 38 are disposed vertically higher than inlet tube 110 and outlet tube 51.

As blood is introduced through inlet 110, it rises first in a direction generally parallel with the surface of bag plate 14, which is in turn parallel with bracket frame 16. After a predetermined amount of blood (e.g., 200 ml.) has entered the bag 12 and bag 12 is contacting bag plate 14 and upper plate 18, further filling requires and results in movement of front plate 18, which in effect causes weighted front plate 18 to "float" on bag 12; during this stage, blood reservoir filling is in a direction basically perpendicular to the surface of bag plate 14. This double direction two-step approach to required blood reservoir filling provides consistent flow dynamics and air handling characteristics at all operating range blood levels. Also, reservoir fluid level is maintained in communication with vents 36, 38 throughout, and bag massage (with possible consequent release downstream of gas microemboli) is minimized. This filling action, plus the contrasting white plastic of bag plate 14, gives excellent low-volume (below 200 ml.) resolution.

The two bypasses and the angled outlet tube inlet surface contribute to this result.

Actually, the magnet 50 and sensor 60 ordinally provide a predetermined lower limit on bag volume by triggering or otherwise providing appropriate signal means when they reach a predetermined distance apart. The angled surface 126, which cooperates with the adjacent bag wall to provide complete cutoff without residual edge passages as when tubing is compressed between two flat surfaces, provides a secondary fail-safe in the event that the magnet and sensor somehow fail to do their job.

What is claimed is:

1. A method of filling a flexible body fluid reservoir with a body fluid, said flexible reservoir having opposing first and second surfaces defining the lateral extent thereof, comprising:

supporting said flexible reservoir on a first lateral member, wherein said first lateral member supportably contacts said first surface of said flexible reservoir substantially across the lateral extent thereof, inclining said first lateral member and flexible reservoir supported thereby to define a bottom end and top end of said flexible reservoir;

positioning an inclined second lateral member over and in predetermined, spaced relation relative to said first lateral member and flexible reservoir supported thereby;

flowing a body fluid into said flexible reservoir, including:
first filling said flexible reservoir until said second surface of said flexible reservoir establishes contact substantially across the lateral extent thereof with said second lateral member, wherein a first predetermined volume of said body fluid is accumulated from said bottom end to said top end of said reservoir; and, following said first filling step, second filling said flexible reservoir to a second predetermined volume, wherein said second lateral member moves away from said first lateral member during said second filling step so that said body fluid accumulates substantially contemporaneously across and substantially throughout the lateral extent of the flexible reservoir.

2. The method of claim 1, said second filling step comprising:

applying a predetermined force with said second lateral member across substantially the entire lateral extent of the second surface of said flexible reservoir to distribute said body fluid therewithin.

3. The method of claim 2, wherein said predetermined force is substantially entirely defined by a weight of said second lateral member contacting said flexible reservoir.

4. The method of claim 1, said flowing step comprising:

introducing said body fluid into said bottom end of said flexible reservoir.

5. The method of claim 1, said step of second filling comprising:

maintaining a predetermined relative angular orientation between said first and second lateral members.

6. The method of claim 1, further comprising a step of:

following said second filling step, removing a portion of said body fluid from said flexible reservoir to change the volume of said body fluid within said flexible reservoir to a third predetermined volume.

7. The method of claim 6, wherein:

said step of flowing a body fluid comprises introducing said body fluid into a first location in said flexible reservoir; and said step of removing a portion of said body fluid comprises flowing a portion of said body fluid through a second location in said flexible reservoir that is below said first location in said flexible reservoir.

8. The method of claim 6, said step of removing a portion of said body fluid further comprising the step of:

automatically terminating said removing step when the volume of said body fluid in the flexible reservoir reaches said third predetermined volume.

9. The method of claim 8, said step of terminating comprising:

sensing when the volume of said flexible reservoir reaches said third predetermined volume and providing a signal in response thereto; and terminating said removing step in response to said signal.

10. The method of claim 1, further comprising a step of:
collecting gas at said top end of said flexible reservoir.

11. The method of claim 10, further comprising a step of:
removing the collected gas from said top end of said flexible reservoir.

12. The method of claim 1, further comprising a step of:
filtering said body fluid by passing said body fluid through a filter element within said flexible reservoir.

13. The method of claim 12, said step of filtering said body fluid comprises:

removing gas bubbles from said body fluid passed through said filter element and collecting said gas bubbles at a top end of said filter element.

14. The method of claim 12, said step of filtering said body fluid comprises:

passing said body fluid toward said bottom end of said flexible reservoir through said filter element to an output tube that provides for removal of said body fluid from said flexible reservoir.

15. The method of claim 12, wherein:

said steps of first and second filling include collecting said body fluid in an unfiltered volume of said flexible reservoir; and said filtering step comprises passing a portion of said body fluid in said unfiltered volume of said flexible reservoir through said filter element to a filtered volume of said flexible reservoir.

16. The method of claim 15, further comprising a step of:
removing a portion of said body fluid in said filtered volume of said flexible reservoir.

17. A method of filling a flexible body fluid reservoir with a body fluid, said flexible reservoir having opposing first and second surfaces defining the lateral extent thereof, comprising:

supporting said flexible reservoir on a first lateral member, wherein said first lateral member supportably contacts said first surface of said flexible reservoir substantially across the lateral extent thereof, inclining said first lateral member and flexible reservoir supported thereby to define a bottom end and top end of said flexible reservoir;

positioning an inclined second lateral member over and in predetermined, spaced relation related to said first lateral member and flexible reservoir supported thereby;

flowing a body fluid into said flexible reservoir, including:
first filling said flexible reservoir until said second surface of said flexible reservoir establishes contact substantially across the lateral extent thereof with said second lateral member, wherein a first predetermined volume of said body fluid is accumulated from said bottom end to said top end of said reservoir; and, following said first filling step, second filling said flexible reservoir to a second predetermined volume with said body fluid by accumulating substantially contemporaneously the body fluid across and substantially throughout the lateral extent of the flexible reservoir, wherein said second lateral member moves away from said first lateral member during said second filling step;

removing a portion of said body fluid to change the volume of said body fluid within said flexible reservoir to a third predetermined volume that is less than said first and second predetermined volumes; and, automatically terminating said removing step when the volume of said body fluid in the flexible reservoir reaches said third predetermined volume, said terminating comprising collapsing one of said first and second surfaces across an inlet portion of an output tube to terminate the removal of said body fluid from said flexible reservoir when the volume of said flexible reservoir reaches said third predetermined volume.

* * * * *